(12) United States Patent
Maahs

(10) Patent No.: US 6,689,149 B2
(45) Date of Patent: *Feb. 10, 2004

(54) ARTERIAL OCCLUDING CANNULA AND METHODS OF USE

(75) Inventor: Tracy D. Maahs, Redwood City, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 372 days.

This patent is subject to a terminal disclaimer.

(21) Appl. No.: 09/799,484

(22) Filed: Mar. 5, 2001

(65) Prior Publication Data

US 2001/0023357 A1 Sep. 20, 2001

Related U.S. Application Data

(63) Continuation of application No. 09/294,533, filed on Apr. 19, 1999, now Pat. No. 6,196,994, which is a continuation of application No. 08/899,606, filed on Jul. 24, 1997, now Pat. No. 5,928,192.

(51) Int. Cl.[7] .............................................. A61M 29/00
(52) U.S. Cl. ..................................... 606/194; 604/96.01
(58) Field of Search ................................. 606/192–194, 606/108, 198; 604/96.01, 101.03, 102.01, 102.02, 102.03, 164.11, 164.13; 600/104; 128/898

(56) References Cited

U.S. PATENT DOCUMENTS

| 4,748,982 A | * | 6/1988 | Horzewski et al. | ....... 604/102.1 |
| 4,909,787 A | | 3/1990 | Danforth | ...................... 604/95 |
| 5,163,905 A | | 11/1992 | Don Michael | ............... 604/101 |
| 5,263,963 A | * | 11/1993 | Garrison et al. | ............. 606/198 |
| 5,312,344 A | | 5/1994 | Grinfeld et al. | ............. 604/101 |
| 5,425,708 A | | 6/1995 | Nasu | ............................. 604/96 |
| 5,618,307 A | | 4/1997 | Donlon et al. | ............... 606/205 |
| 5,820,593 A | | 10/1998 | Safar et al. | .................... 604/96 |
| 5,833,650 A | | 11/1998 | Imran | .......................... 604/53 |
| 6,048,331 A | | 4/2000 | Tsugita et al. | ................ 604/96 |
| 6,090,097 A | | 7/2000 | Barbut et al. | ................ 604/511 |
| 6,196,994 B1 | * | 3/2001 | Maahs | ...................... 604/96.01 |

FOREIGN PATENT DOCUMENTS

| EP | 0218275 | 4/1987 |
| WO | WO98/39046 | 9/1998 |

* cited by examiner

Primary Examiner—Julian W. Woo
(74) Attorney, Agent, or Firm—O'Melveny & Myers LLP; John Christopher James

(57) ABSTRACT

A balloon occlusion device for aspirating embolic material from a blood vessel, such as from the aorta during cardiac surgery. The device includes an arterial cannula having a proximal end adapted to receive blood from a bypass-oxygenator machine, a distal end adapted to enter an artery, and a blood flow lumen extending between the proximal end and an outlet on the distal end. The cannula has an aspiration port proximate to the outlet, which communicates with an aspiration lumen. The cannula also includes an inflatable balloon attached to the cannula between the outlet and the aspiration port and capable of assuming an inflated condition for occluding a blood vessel. To use the device, the distal end of the cannula is introduced into a blood vessel, such as the aorta, the outlet is oriented downstream for delivering blood, and the balloon is inflated to occlude the vessel. Fluid may then be flushed into and aspirated out through the aspiration port as desired to remove loose embolic material from the vessel upstream of the balloon. Optionally, the device may include a second deployable balloon for further occluding the vessel at a second location.

20 Claims, 2 Drawing Sheets

ARTERIAL OCCLUDING CANNULA AND METHODS OF USE

This is a continuation of U.S. application Ser. No. 09/294,533, filed Apr. 19, 1999 now U.S. Pat. No. 6,196,994, which is a continuation of U.S. application Ser. No. 08/899,606, filed Jul. 24, 1997, now U.S. Pat. No. 5,928,192, the contents of both of which are fully incorporated herein by reference.

FIELD OF THE INVENTION

The present invention relates generally to devices for removing embolic material from blood vessels, and, more particularly, to an occlusion device (e.g., a balloon) for aspirating a blood vessel, such as the aorta during cardiac surgery, to remove embolic material from the vessel, and to methods of using such a device.

BACKGROUND

During cardiac surgery, it is often necessary to introduce a cannula into an artery or other blood vessel. For example, an arterial cannula is typically introduced into the aorta to deliver blood from a bypass-oxygenator machine during cardiopulmonary bypass (CPB), as is used during coronary arterial bypass surgery and other procedures. Such a cannula generally includes a proximal end for receiving blood from the bypass-oxygenator machine, a distal end for entry into the artery, and a lumen extending between the proximal and distal ends.

One concern with such procedures is that calcified plaque or other embolic material may be dislodged during the procedure, particularly when clamping or unclamping the aorta. See Barbut et al., "Cerebral Emboli Detected During Bypass Surgery Are Associated With Clamp Removal," Stroke, 25(12):2398–2402 (1994), incorporated herein by reference in its entirety, which quantifies the level of embolic release during each step of CPB and explains when protection from embolization is needed. Such embolic material may travel downstream, possibly becoming lodged in another portion of the blood vessel or possibly reaching a vital organ, such as the brain, where the material can cause substantial injury to the patient.

In response to this concern, a blood filter device may be introduced into the blood vessel to capture any embolic material that becomes dislodged within the vessel. For example, a blood filter may be disposed on the distal end of an arterial cannula for capturing embolic material in the vessel into which the cannula is introduced. Filters, however, may have certain disadvantages because as blood flows through the filter, the blood may clot and attach to the filter mesh, possibly impairing flow through the filter, and consequently through the vessel. In addition, the filter may become clogged with embolic material during use, preventing the device from effectively capturing additional material and/or impairing flow through the vessel.

Accordingly, there appears to be a need for a device for removing embolic material from a blood vessel, such as the aorta, that avoids these problems.

SUMMARY OF THE INVENTION

The present invention is directed to a device for aspirating embolic material from a blood vessel, such as from the aorta during cardiac surgery, and also from the common carotid artery, external and internal carotid arteries, brachiocephalic trunk, middle cerebral artery, anterior cerebral artery, posterior cerebral artery, vertebral artery, basilar artery, subclavian artery, brachial artery, axillary artery, iliac artery, renal artery, femoral artery, popliteal artery, celiac artery, superior mesenteric artery, inferior mesenteric artery, anterior tibial artery, posterior tibial artery and all other arteries carrying oxygenated blood. In a first preferred embodiment, the device is an arterial cannula with an occlusion device (e.g., a balloon occluder) capable of aspirating a blood vessel and thereby removing embolic material from the vessel. The cannula is a substantially rigid elongate member having a proximal end adapted to receive blood from a bypass-oxygenator machine, a distal end adapted to enter an artery, and a blood flow lumen extending between the proximal end and an outlet on the distal end.

The cannula has an aspiration port proximate to the outlet, which communicates with an aspiration lumen that extends proximally from the aspiration port along the cannula. The cannula also includes an inflatable balloon attached to the cannula between the outlet and the aspiration port, the balloon being capable of assuming an inflated condition for occluding a blood vessel.

To use the device, the distal end of the cannula is introduced into a blood vessel, such as into the ascending aorta upstream of the carotid arteries. The outlet is oriented downstream for delivering blood into the vessel from a bypass-oxygenator machine. The balloon on the cannula is then inflated to occlude the vessel, that is, the balloon expands and engages the wall of the vessel, thereby providing a fluid-tight seal between an upstream portion and a downstream portion of the vessel. Fluid may then be introduced through the aspiration port into the upstream portion of the vessel, sweeping up loose embolic material within the upstream portion. The fluid may then be withdrawn from the upstream portion of the vessel through the aspiration port, for example by connecting the aspiration lumen to hospital suction, thereby aspirating loose embolic material from the upstream portion of the vessel.

In a second preferred embodiment, the device includes an arterial cannula, a first balloon occluder attached to the cannula, and an aspiration port, similar to the embodiment described above. In addition, the device also includes a second balloon occlusion device deployable from the distal end of the cannula, the second balloon also being capable of assuming an inflated condition for further occluding a blood vessel. Preferably, the second balloon is attached to the distal end of an elongate tubular member. The elongate tubular member is slidably received in the aspiration lumen, allowing the second balloon to slidably deployed from and retracted into the aspiration port. Alternatively, a separate lumen may be provided in the cannula for the second balloon occlusion device.

Similar to the previous embodiment, the distal end of the cannula is introduced into a blood vessel, and the outlet is oriented downstream. The first balloon is inflated to occlude the vessel, and substantially isolate an upstream portion of the vessel from a downstream portion.

The second balloon may then be deployed into the upstream portion of the vessel, for example into the aorta towards the coronary arteries. The second balloon may then be inflated to further occlude the blood vessel, and substantially isolate the upstream portion, for example from the coronary arteries, to prevent fluid and/or embolic material from traveling upstream when the upstream portion is flushed.

Fluid may then be flushed into the vessel and aspirated out through the aspiration port as desired to remove loose embolic material from the upstream portion of the vessel. The second balloon may then be deflated, and withdrawn back into the cannula. Upon completion of the procedure, the first balloon may be deflated, and the cannula removed from the vessel.

Thus, a device in accordance with the present invention allows a blood vessel to be dammed downstream from a location in which emboli are likely to be dislodged during the course of a surgical procedure. The region of the vessel upstream of the dam may then be flushed and aspirated as desired, thereby removing embolic material released during the procedure and preventing the embolic material from escaping downstream and potentially injuring the patient.

An additional feature of a balloon occlusion device in accordance with the present invention is that the balloon may serve an additional function besides damming the vessel to allow loose embolic material to be aspirated away. The balloon may substantially engage the walls of the vessel and provide a fluid-tight seal, thereby eliminating the need for other devices to block the vessel, such as a cross clamp which is often used to clamp the aorta during cardiac surgery.

Accordingly, it is an object of the present invention to provide a balloon occlusion device for aspirating embolic material from a blood vessel, which avoids many of the problems of previously known devices, such as blood filters.

Other objects and features of the present invention will become apparent from consideration of the following description taken in conjunction with the accompanying drawings.

DETAILED DESCRIPTION OF THE PREFERRED EMBODIMENTS

Figure 1:
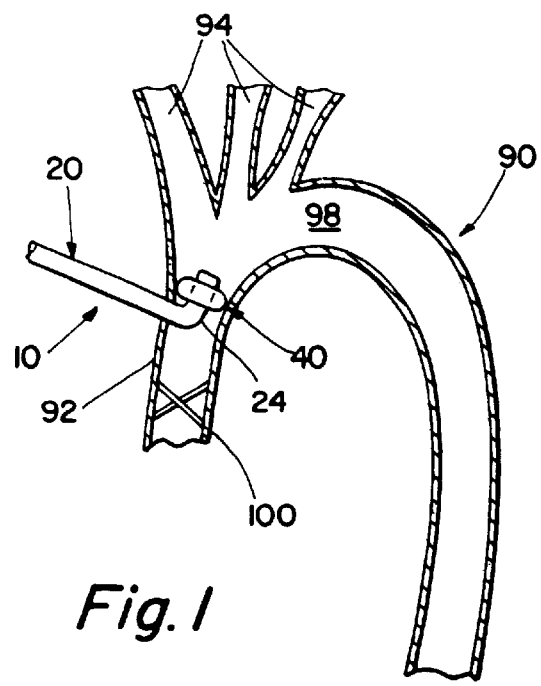
FIG. 1 is a cross-sectional view of a cannula with balloon occluder in accordance with the present invention introduced into the ascending aorta of a patient.
Figure 2:
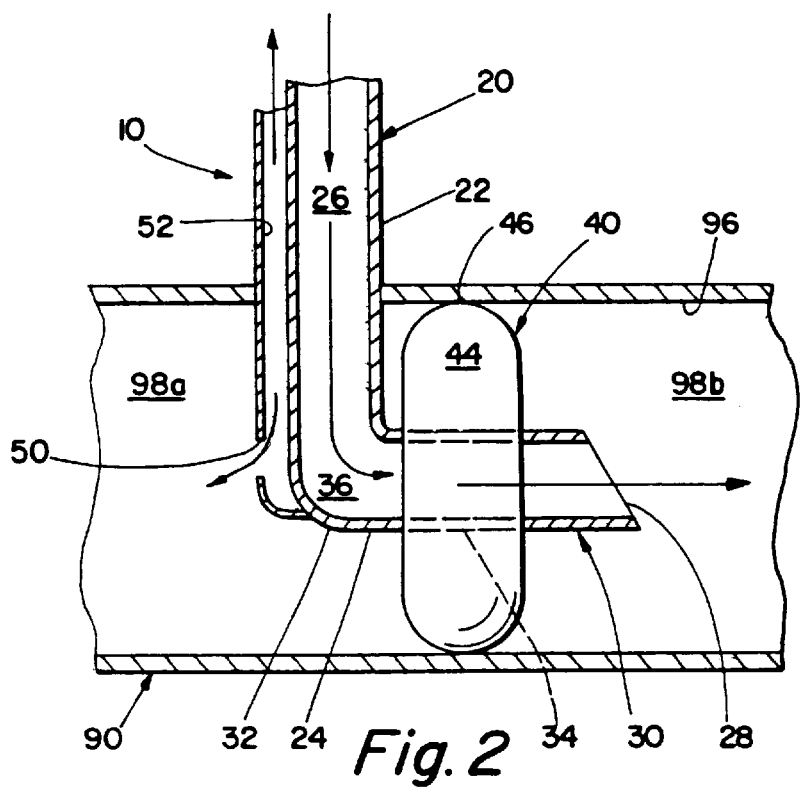
FIG. 2 is a cross-sectional detail of the cannula of FIG. 1 with the balloon inflated to occlude a blood vessel.

Turning now to the drawings, FIGS. 1 and 2 show a preferred embodiment of a device 10 for aspirating embolic material from a blood vessel. The device 10 includes an aortic cannula 20, a balloon occluder or dam 40 and an aspiration port 50. The cannula 20 is an elongate tubular member 22, having a proximal end (not shown), a distal end 24, and a lumen 26 which extends between the proximal and distal ends 24. The proximal end is adapted for receiving blood from a bypass-oxygenator machine (not shown). The distal end 24 has a tapered, curved and/or rounded end adapted to enter an artery, and includes an outlet 28 communicating with the lumen 26. The cannula 20 is generally formed from a substantially rigid material, such as conventional medically suitable plastic or rubber materials, appropriate for aortic cannulation devices.

The distal end 24 preferably also includes a curved or lateral outlet portion 30 that extends substantially perpendicularly to the longitudinal axis of the elongate tubular member 22 and has the outlet 28 thereon. The proximal edge 32 of the outlet portion 30 is preferably rounded and/or curved to facilitate introduction into a blood vessel. The outlet portion 30 also includes a curved lumen 36 extending between the lumen 26 in the cannula 20 and the outlet 28, the lumen 36 preferably being radiused to minimize the risk of hemolysis or other problems which may be caused by an abrupt change in direction of blood flow.

The balloon occluder 40 is an inflatable balloon 42 attached to the cannula 20, preferably to the outer surface 34 of the outlet portion 30 adjacent to the outlet 28. The balloon 42 has an annular shape capable of assuming an inflated condition for occluding or damming a blood vessel into which the device 10 is introduced. The inflatable space 44 within the balloon 42 communicates with an inflation lumen (not shown) that extends proximally along the cannula 20 towards the proximal end thereof. A source of inflation media (not shown), such as saline, may be directed into and out of the inflation lumen, preferably from the proximal end of the cannula 20 to inflate and deflate the balloon 42.

The cannula 20 also includes an aspiration port 50, preferably adjacent the proximal edge 32 of the outlet portion 30. The aspiration port 50 communicates with an aspiration lumen 52 for aspirating and/or flushing the vessel. Preferably, the aspiration lumen 52 extends proximally along the cannula 20 towards the proximal end thereof. A source of fluid for flushing the vessel, such as saline, and a source of vacuum, such as hospital suction, may be switchably connected to the aspiration lumen 52, preferably at the proximal end of the cannula 20. Alternatively, a separate lumen (not shown) for introducing fluid into the vessel may be provided in addition to the aspiration lumen 52. Each of the lumens, that is, the blood flow lumen 26, the aspiration lumen 52 and the inflation lumen (not shown) are substantially isolated from one another throughout their lengths.

Generally, the aspiration port 50 is located proximal of the outlet 28, and the balloon occluder 40 is mounted between the aspiration port 50 and the outlet 28. Thus, the distal end 24 of the cannula 20 may be oriented within a blood vessel such that the outlet 28 is directed in a downstream direction, and the aspiration port 50 is located upstream of the outlet 28.

As shown in FIGS. 1 and 2, the device 10 may be particularly useful for aspirating a vessel such as the aorta 90, that is, for removing embolic material from the ascending aorta 92, to prevent embolic material from traveling downstream, especially into the carotid arteries 94 and possibly to the brain (not shown) where embolic material may cause substantial damage. The distal end 24 of the cannula 20 is introduced into the vessel 90 using conventional procedures providing thorascopic access to the vessel. For example, a thoracotomy may be performed to create a passage into the patient's chest and into the vessel, through which the cannula 20 may be introduced. The outlet 28 is directed downstream to allow blood to be delivered through the blood flow lumen 26 into the vessel 90 from a bypass-oxygenator machine (not shown).

The balloon 42 is inflated until the outer periphery 46 of the balloon 42 substantially engages the wall 96 of the vessel 90, thereby providing a fluid-tight seal and damming the lumen 98 of the vessel 90. The inflated balloon 42 may provide a sufficient seal, for example, such that the balloon 42 may be used instead of a cross clamp to clamp the aorta 90 during a coronary bypass procedure. Alternatively, a cross clamp 100 may be provided to clamp the aorta 90, as described below.

The inflated balloon 42 divides the lumen 98 of the vessel 90 into an upstream portion 98a and a downstream portion 98b that are substantially isolated from one another. If a separate clamp 100 is used, the ascending aorta 92 may then be clamped upstream of the balloon 42 in preparation for cardiac surgery, possibly dislodging embolic material from the wall 96. Any material released will be retained in the upstream portion 98a of the aorta 90, unable to travel downstream because of the inflated balloon 42.

At any time when the balloon 42 is fully inflated and damming the vessel 90, fluid, such as saline, may be introduced through the aspiration port 50 into the upstream portion 98a, for example, from a source attached to the aspiration lumen 52 at the proximal end of the cannula 20. The fluid may enter the upstream portion 98a and flush any loose embolic material therein. Suction may then be provided through the aspiration lumen 52, removing the fluid and loose embolic material from the upstream portion 98a, into the aspiration port 50 and out the aspiration lumen 52. The process of flushing and aspirating the upstream portion 98a of the aorta 90 may be repeated as often as desired during the procedure to remove loose embolic material therein and/or to dislodge additional embolic material, for example which may be caught between the balloon 42 and the wall 96 of the vessel 90.

Of particular concern during cardiac surgery, embolic material may be released when the aorta is clamped and unclamped, or when the heart and/or aorta are manipulated. The device 10 allows the upstream portion 98a to be flushed and aspirated as often as desired before the end of the procedure, without concerns about impairing flow through the vessel 90 as may occur when a blood filter device is used. The balloon 42 may then be deflated, allowing resumed blood flow through the vessel 90, and the cannula 20 may then be removed using conventional procedures.

Figure 3:
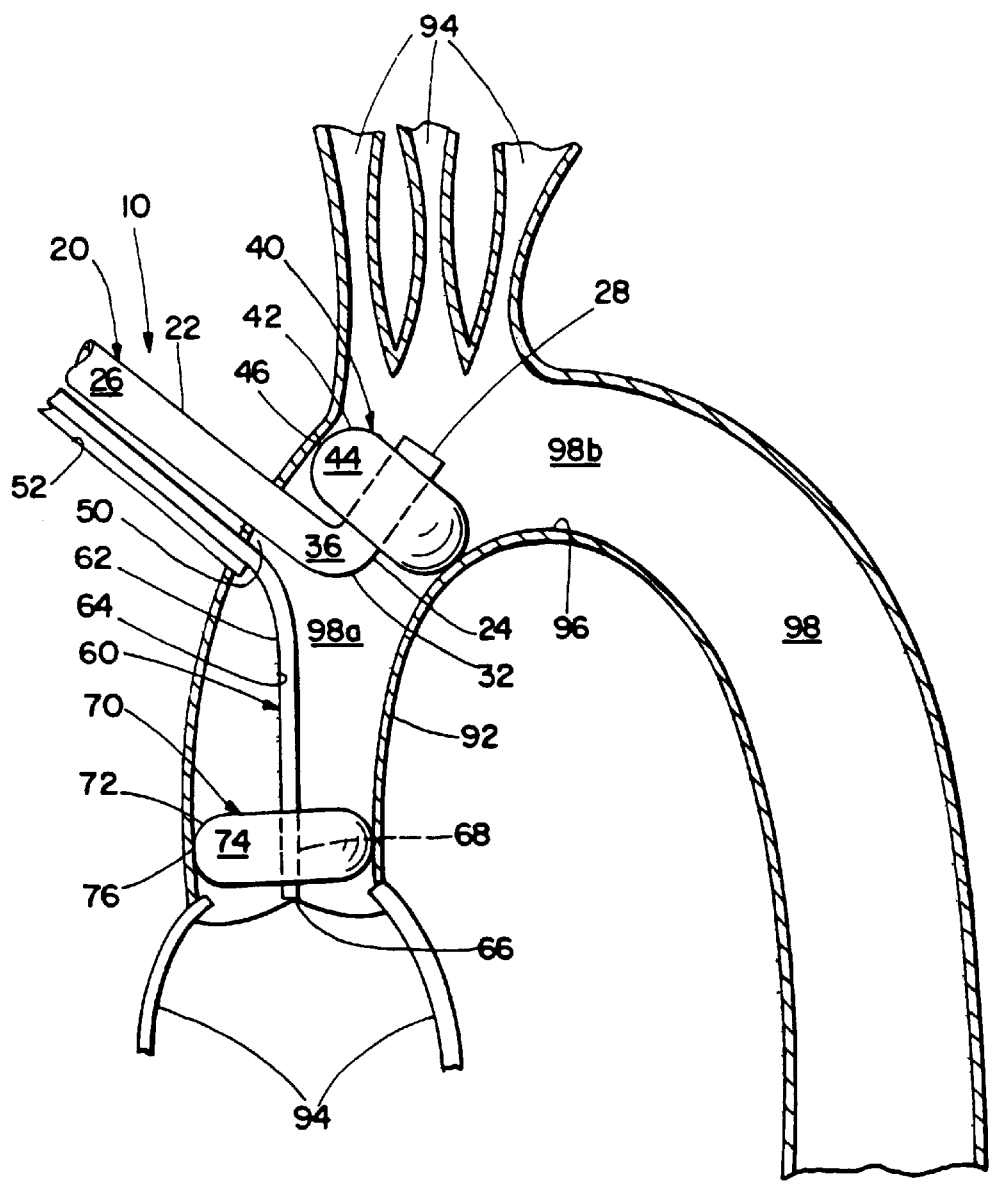
FIG. 3 is a cross-sectional view of another embodiment, including a second balloon occluder introduced into the ascending aorta.

Turning now to FIG. 3, a second embodiment of a device 10 in accordance with the present invention is shown. Similar to the previously described embodiment, the device 10 includes an arterial cannula 20, a first balloon occluder 40 and an aspiration port 50. In addition, the device 10 includes a second balloon occlusion device 60. Preferably, the occlusion device 60 is provided as part of and is deliverable from the cannula 20, although alternatively the occlusion 60 may be deployed from a separate cannula (not shown) that may be introduced into the vessel upstream of the by-pass cannula 20.

The occlusion device 60 includes an elongate tubular member 62 and a second balloon occluder 70. The tubular member 62 has a proximal end (not shown), a distal end 66, and preferably includes a lumen 64 extending between the proximal end (not shown) and the distal end 66, for example for providing a cardioplegia port for cardiac procedures. The tubular member 62 may be formed from a semi-rigid and/or resilient material, such as plastic or metal, that facilitate introduction of the occlusion device 60 into the vessel 90.

The second balloon occluder 70, similar to the first balloon occluder 40, includes an inflatable balloon 72 capable of assuming an inflated condition for damming the lumen of a vessel. Preferably, the second balloon 72 has an annular shape, and is attached to the outer surface 68 of the tubular member 62 adjacent the distal end 66 thereof. The inflatable space 74 within the balloon 72 communicates with an inflation lumen (not shown) that preferably extends proximally along the tubular member 62 to a conventional source of an inflation media, for example on the proximal end of the tubular member 62.

The second occlusion device 60 is generally slidably received in the cannula 20. Preferably, the distal end 66 of the tubular member 62 is inserted into the aspiration lumen 52 at the proximal end of the cannula 20 and directed distally until it reaches the aspiration port 50. The tubular member 62 may have a diameter substantially smaller than the aspiration lumen 52, thereby allowing fluid to be flushed and aspirated through the lumen 52, even with the tubular member 62 extending therethrough. Alternatively, the cannula 20 may include a separate lumen (not shown) for the second occlusion device 60.

Once the cannula 20 is introduced into a vessel, the second occlusion device 60 may be deployed into the vessel to further dam the vessel. For example, the second occlusion device 60 may be particularly useful in a cardiac surgical procedure for removing loose embolic material within the aorta. The cannula 20 is introduced into a vessel 90, such as the ascending aorta 92, with the outlet 28 directed downstream, for delivery of blood into the vessel 90 from a bypass-oxygenator machine, similar to the embodiment described above. The first balloon 42 is inflated to dam the vessel 90, and provide a substantially fluid-tight seal between the upstream portion 98a of the vessel 90 and the downstream portion 98b into which the blood is delivered. The second occlusion device 60 may then be introduced into the upstream portion 98a, for example towards the coronary arteries 99. Once in a desired position, such as above the coronary arteries 99, the second balloon 72 may be inflated to dam the vessel 90 further, for example, to seal the upstream portion 98a from the coronary arteries 99.

During the procedure at any time prior to deflating the first balloon 42, fluid may be flushed into the upstream portion 98a of the vessel 90 from the aspiration port 50 for removing embolic material. The second balloon occluder 70 prevents the fluid, and consequently any embolic material, from entering the coronary arteries 99. The fluid may be suctioned from the upstream portion 98a into the aspiration lumen 50, removing loose embolic material. Towards the end of the procedure, the second balloon 72 may be deflated, and the occlusion device 60 may be withdrawn back into the aspiration lumen 52. If desired, fluid may be flushed into and/or aspirated from the upstream portion 98a subsequent to deflation of the second balloon 72, to remove additional embolic material that may be dislodged during deflation. The first balloon 42 may then be deflated, and the cannula 20 removed from the vessel 90.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. An arterial cannula comprising:
   an elongate tubular member having a proximal end adapted to receive blood from a bypass-oxygenator machine, a distal end adapted to enter an artery, and a blood flow lumen extending between the proximal end and an outlet on the distal end, wherein the distal end includes a curved portion extending substantially perpendicularly to a longitudinal axis of the cannula;
   a port proximal the curved portion of the distal end on the cannula proximate to the outlet, the port communicating with a second lumen that extends proximally from the port along the cannula; and
   a medical device adapted for insertion through the second lumen and beyond the port into the aorta.

2. The arterial cannula of claim 1, wherein the medical device comprises an elongate tubular member having an expandable occluder on a distal end.

3. The arterial cannula of claim 2, wherein the expandable occluder comprises an inflatable balloon.

4. The arterial cannula of claim 3, wherein the inflatable balloon has an annular shape and is sealed to the outer wall of the medical device.

5. The arterial cannula of claim 1, wherein the radius of the blood flow lumen is sized to minimize the risk of hemolysis.

6. The arterial cannula of claim 1, wherein the two lumens are substantially isolated from one another.

7. An arterial cannula for aspirating a blood vessel and thereby removing loose embolic material within the vessel, the arterial cannula comprising:

a cannula having a proximal end adapted to receive blood from a bypass-oxygenator machine, a distal end adapted to enter an artery, a blood flow lumen and an aspiration lumen, each lumen extending between a proximal portion of the cannula and the distal end thereof and being substantially isolated from one another, wherein each lumen is adapted to extend out of the blood vessel when the cannula is deployed;

an aspiration port on the distal end communicating with the aspiration lumen;

a blood flow outlet on the distal end communicating with the blood flow lumen; and a medical device adapted for insertion through the aspiration lumen and beyond the aspiration port into the blood vessel.

8. The arterial cannula of claim 7, wherein the blood flow outlet is located on a downstream portion of the distal end, and the aspiration port is located on an upstream portion of the distal end.

9. The arterial cannula of claim 7, wherein the medical device comprises an elongate tubular member having an expandable occluder on a distal end.

10. The arterial cannula of claim 9, wherein the expandable occluder comprises an inflatable balloon.

11. The arterial cannula of claim 10, wherein the inflatable balloon has an annular shape and is sealed to the outer wall of the medical device.

12. The arterial cannula of claim 7, wherein the radius of the blood flow lumen is sized to minimize the risk of hemolysis.

13. A method for occluding the aorta, said method comprising the steps of:

providing a cannula having an outlet and a port on its distal end, the outlet on the opposite side of the catheter from the port;

introducing the distal end of the cannula into the aorta;

orienting the outlet in a downstream direction within the aorta, thereby orienting the port in an upstream direction;

introducing a medical device through the port into the aorta; and deploying the medical device into the aorta towards the coronary arteries.

14. The method of claim 13, wherein the medical device comprises an elongate catheter having a first expandable occluder on a distal end, and wherein the method further comprises the step of expanding the first expandable occluder to occlude the aorta, thereby isolating the coronary arteries from a position downstream of the expandable occluder.

15. The method of claim 14, wherein the first expandable occluder comprises an inflatable balloon.

16. The method of claim 14, comprising the additional step of delivering blood through the outlet downstream of the first expandable occluder.

17. The method of claim 14, wherein the cannula comprises a second expandable occluder mounted axially around its distal end between the outlet and the port, and wherein the method comprises the additional step of expanding the second expandable occluder to form a second occlusion of the aorta downstream of the first expandable occluder, thereby isolating a region within the aorta from the first expandable occluder to the second expandable occluder.

18. The method of claim 17, further comprising the steps of:

introducing aspiration fluid through the port into the isolated region; and withdrawing the aspiration fluid through the port, thereby aspirating loose embolic material from the isolated region.

19. The method of claim 13, wherein the cannula is introduced into the aorta by thorascopic access.

20. The method of claim 13, wherein the cannula is introduced into the aorta by direct access.

\* \* \* \* \*